(12) United States Patent
Edwards et al.

(10) Patent No.: US 6,387,326 B1
(45) Date of Patent: May 14, 2002

(54) AUTOMATED SLIDE STAINING SYSTEM AND METHOD THEREOF

(75) Inventors: Peter S. Edwards, Tallahassee, FL (US); A. John Bertolino, Blairsville, PA (US); Jerry C. Premus, Scottdale, PA (US); Lloyd Seager, Greensburg, PA (US)

(73) Assignee: Fisher Scientific Company L.L.C., Pittsburgh, PA (US)

( * ) Notice: Subject to any disclaimer, the term of this patent is extended or adjusted under 35 U.S.C. 154(b) by 0 days.

(21) Appl. No.: 09/418,262

(22) Filed: Feb. 9, 2000

(Under 37 CFR 1.47)

Related U.S. Application Data

(63) Continuation-in-part of application No. 08/995,461, filed on Dec. 20, 1997, now Pat. No. 6,076,583, and a continuation-in-part of application No. 08/277,170, filed on Jul. 19, 1994, now Pat. No. 5,700,346.

(51) Int. Cl.[7] .......................... G01N 21/00; B01L 3/00; B32B 31/00; B31F 5/00; B65C 9/08
(52) U.S. Cl. .......................... 422/63; 422/99; 156/539; 156/556; 156/570; 414/416.04
(58) Field of Search .......................... 422/100, 99, 62, 422/63, 64, 65; 156/357, 356, 556, 363, 364, 539, 57, 360, 578; 118/58, 64, 326, 401, 425; 414/416.04, 416.11, 331.17

(56) References Cited

U.S. PATENT DOCUMENTS

| | | | |
|---|---|---|---|
| 3,431,886 A | 3/1969 | McCormick et al. | |
| 3,823,845 A | 7/1974 | Mott, Sr. et al. | |
| 3,892,197 A | 7/1975 | Kinney et al. | |
| 3,903,908 A | 9/1975 | Logue et al. | |
| 3,939,019 A | 2/1976 | Pickett | |
| 4,092,952 A | 6/1978 | Wilkie et al. | |
| 4,151,809 A | 5/1979 | Johnson | |
| 4,190,420 A | * 2/1980 | Covington et al. | 422/63 |
| 4,190,472 A | 2/1980 | Slonicki | |
| 4,219,529 A | 8/1980 | Tersteeg et al. | |
| 4,482,282 A | * 11/1984 | Wildmoser | 414/404 |
| 4,537,648 A | 8/1985 | Shiino et al. | |
| 4,651,671 A | 3/1987 | Pederson | |
| 4,738,824 A | 4/1988 | Takeuchi | |
| 4,936,465 A | 6/1990 | Zold | |
| 5,496,517 A | * 3/1996 | Pfost et al. | 422/63 |
| 5,653,942 A | * 8/1997 | Terashima et al. | 422/63 |
| 5,670,375 A | * 9/1997 | Seaton et al. | 436/48 |
| 5,674,454 A | * 10/1997 | Karl et al. | 422/63 |
| 5,692,867 A | * 12/1997 | Kondo et al. | 414/268 |
| 5,700,346 A | 12/1997 | Edwards | |
| 5,736,101 A | * 4/1998 | Gianino | 422/65 |

(List continued on next page.)

OTHER PUBLICATIONS

Supplementary Partial European Search Report for Application No. EP 95 93 6781.

Patent Abstracts of Japanese Patent No 60 011136 dated Jun. 20, 1983 for Method and Device for Dyeing Microscope Specimen.

Primary Examiner—Jill Warden
Assistant Examiner—Brian R. Gordon
(74) Attorney, Agent, or Firm—Rader, Fishman & Grauer PLLC

(57) ABSTRACT

The present invention relates to an automatic slide staining system that will process stained slides, such as cytology or histology specimens. The invention includes a slide storage device, a slide transport apparatus, and a first platen including a plurality of staining stations. The stained slides are placed in the storage device and then are removed and processed at various stations via the transport apparatus. The invention can be altered so that a cover slip apparatus can be incorporated within the system. This permits a cover slip to be placed on the stained slide after a complete transverse of the slide staining stations.

16 Claims, 7 Drawing Sheets

U.S. PATENT DOCUMENTS

| | | | | |
|---|---|---|---|---|
| 5,854,075 A | * | 12/1998 | Levine et al. | 436/46 |
| 6,001,670 A | * | 12/1999 | Mochida et al. | 438/111 |
| 6,017,495 A | * | 1/2000 | Ljungmann | 422/65 |
| 6,033,932 A | * | 3/2000 | Mochida et al. | 438/111 |
| 6,074,617 A | * | 6/2000 | DeYoung et al. | 422/104 |
| 6,076,583 A | * | 6/2000 | Edwards | 156/539 |

* cited by examiner

AUTOMATED SLIDE STAINING SYSTEM AND METHOD THEREOF

This application is a c-i-p of U.S. patent application Ser. No. 08/277,170 filed on Jul. 19, 1994, now U.S. Pat. No. 5,700,346 and Ser. No. 08/995,461 filed on Dec. 20, 1997, now U.S. Pat. No. 6,076,583.

BACKGROUND OF THE INVENTION

1. Field of the Invention

The present invention relates to a system for staining slides of human tissue specimens, and more particularly for staining histology and cytology tissue specimens on a slide for subsequent microscopic examination.

2. Description of the Background Art

Throughout the United States steps are being taken to improve Slide Staining Systems for subsequent pathologic examination in medical laboratories and hospitals. The primary cost component of preparing and staining a slide is labor. Accordingly, many efforts have been devoted to reduce the labor cost component of preparing a slide. With the advent of cost containment throughout the health-care industry, renewed efforts are being made to examine all direct labor cost areas with a focus on reducing the amount of labor heretofore involved, and the associated cost.

For example, U.S. Pat. No. 4,190,472 issued to Slonicki, discloses an automated system for the application of cover glasses on histological and cytological slides. Patent '472 discloses a processing area wherein a slide that has been stained previously is progressively turned 90 degrees to mate with a cover glass to insure a contamination free tissue specimen.

Patent '472 also disclosed a device for depositing glue on the stain slide and a device for applying the cover glass to the glued portion of the slide. Patent '472 is silent of the use of a fume extractor to remove noxious and harmful fumes from the apparatus, which could cause a reduction in the quality of the surrounding environment, where other lab personnel are working.

U.S. Pat. No. 3,939,019 issued to Pickett disclosed an apparatus for covering a slide with a tape material. Patent '019 teaches away from the use of a cover glass to seal the specimen and maintain the specimen in a contamination free environment.

U.S. Pat. No. 4,936,465 issued to Zold discloses an apparatus for dispensing a staining fluid. Patent '465 does not teach or suggest using the apparatus for sealing the stained slide with any type of optically correct transparent material. Patent '465 further is silent to the use of a fume extractor for cleaning the toxic and noxious gases generated in the staining process and removing potentially harmful compounds from the environment which could be harmful to laboratory workers who are adjacent to or in proximity to the slide staining apparatus.

None of these previous efforts, however, provide the benefits intended with the present invention. Additionally, prior techniques do not suggest the present inventive combination of component elements as disclosed and claimed herein. The present invention achieves its intended purposes, objectives and advantages over the prior art device through a new, useful and non-obvious combination of component elements, which is simple to use, with the utilization of a minimum number of functioning parts, at a reasonable cost to manufacture, assemble, test and by employing only readily available material.

SUMMARY OF THE INVENTION

The present invention provides an automatic staining system for which will successfully and efficiently process stained slides, such as cytology or histology specimens. This system of the present invention enables the stain slide to be process and includes an alternative embodiment for enabling a cover slip to be secured thereto. Such versatility in an apparatus will provide a system, which is accurately and effectively process, any specimen on a stained slide. This system of the present invention is so design so as to minimize the amount of material used during conventional process as well as provide a system which will distribute solution, used in the staining process, thoroughly and without trapping air therein.

In one embodiment of the present invention, the system is used to process slides and provides a protective layer thereon, once the slide has been process. In this embodiment, the system of the present invention includes a slide storage device, a slide transport apparatus, a processing platen including a plurality of staining stations, and a heating station.

The slides to be processed are stored in the slide storage device. Upon activation of the apparatus, the slides are expelled, one at a time, for processing via the slide transport apparatus. This transport apparatus further enables the slides to be carried onto the staining stations for processing.

The last dispensing station on the processing platen releases a resin solution. From this dispensing station, the slide is guided to a heating station. At this time the resin coating, which was applied at the last dispensing station, is dried. This will provide for the slide to have a protective resin coating. After the resin has dried, the slide will be dropped into a slide receptacle.

The embodiment described above can be altered slightly so that a cover slip apparatus can be incorporated within the system. In order to do so, the heating station is removed. A Cover slip dispensing apparatus replaces the heating station. In this configuration a cover slip is applied directly after the staining of the particular slide. As desirable, this particular arrangement will intrinsically offer more protection to the processed specimen.

Accordingly, it is the object of the present invention to provide for a staining system that will process stained slides efficiently and effectively and which will overcome the deficiencies, drawbacks, and shortcomings of prior staining apparatus and methods thereof.

It is another object of the present invention to provide for a staining system which will process stained slides and encapsulate the specimen on a slide in a sterile and contaminant free environment while utilizing minimal laboratory labor.

Still another object if the present invention is to provide a slide staining system that will successfully eliminate any potential for cellular contamination between slides during the staining process this will result in preventing the tissue specimen to be in direct communication with the slide staining apparatus for inherently preventing any cross contamination of specimens between successive slides.

A further object of the present invention to provide a slide staining system that removes all the toxic and noxious fumes generated in the slide staining process from the surrounding environment in order to reduce the adverse effect on laboratory personnel.

It is yet another object of the present invention to provide a slide staining system that can quickly be converted from histological specimens to cytological specimens with minimal downtime and minimal conversion effort.

Still a further object of the present invention, to be specifically enumerated herein, is to provide a slide staining system in accordance with the proceeding objects and which will conform to conventional forms of manufacture, be of simple construction and easy to use so as to provide a device that would be economically feasible, long lasting and relatively trouble free in operation.

Although there have been many inventions related to a slide staining system none of the inventions have become sufficiently compact, low cost and reliable enough to become commonly used. The present invention meets the requirements of the simplified design, compact size, low initial cost, low operating cost, ease of installation and maintainability, and minimal amount of training to successfully employ the invention.

The foregoing has outlined some of the more pertinent objects of the invention. These objects should be construed to be merely illustrative of some of the more prominent features and application of the intended invention. Many other beneficial results can be obtained by applying the disclosed invention in a different manner or modifying the invention within the scope of the disclosure. Accordingly, other objects and a fuller understanding of the invention may be had by referring to the detailed description of the preferred embodiments in addition to the scope of the invention defined by the claims taken in conjunction with the accompanying figures.

BRIEF DESCRIPTION OF THE DRAWINGS

Similar reference numerals refer to similar parts throughout the several views of the figures.

DESCRIPTION OF THE PREFERRED EMBODIMENTS

Figure 1:
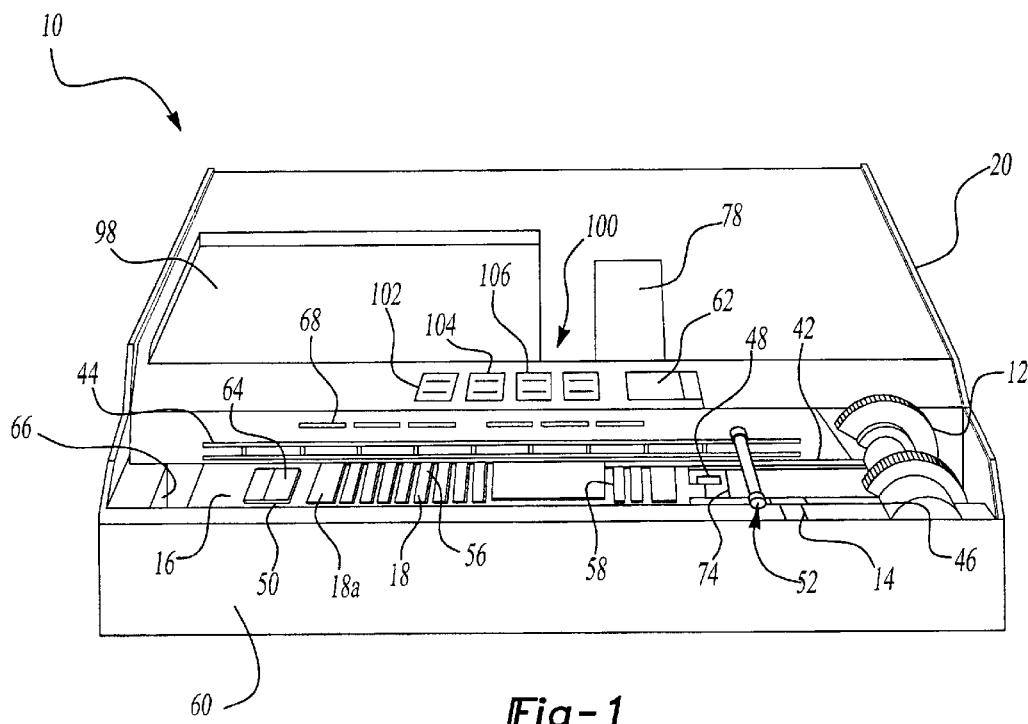
FIG. 1 is a perspective view of the automated slide staining system of the present invention.
Figure 2:
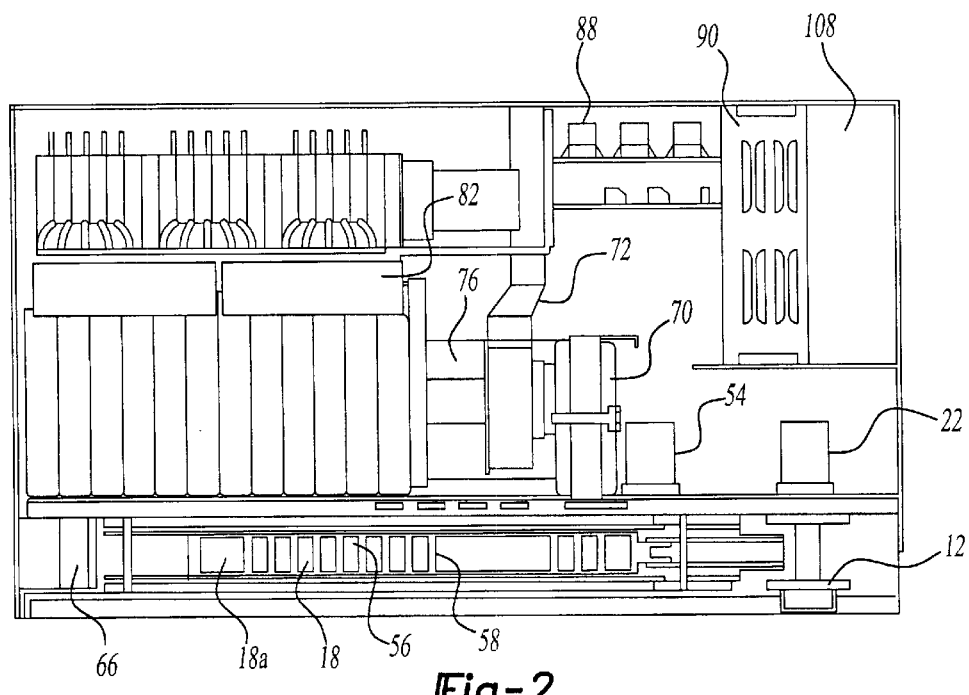
FIG. 2 is a top view of the automated slide staining system of the present invention.

With reference to the drawings, in particular to FIGS. 1 and 2, the present invention will be described. As seen in these figures, the present invention is an automatic slide staining system 10 comprising a slide storage device 12, a slide transport apparatus 14, and a processing platen 16 including a plurality of staining stations 18.

The slide storage device 12 is designed and configured to removably receive slides (not illustrated), such as cytology or histology. As such, this slide storage device 12 is removably secured to the base of the system. The slide storage device, also known as a carousel, is illustrated in further detail in FIGS. 1, 2, and 3. When secured, the slide storage device 12 will be disposed in a horizontal position, as seen in FIGS. 1 and 2.

This slide storage device or carousel 12 is removably secured to a shaft (not illustrated) of a first motor (stepper motor) 22. Once the machine is activated, the first motor is initiated to provide for the shaft to rotate. The slides are then individually discharged onto slide transport apparatus 14 in order to be processed on the various stations 18 of the processing platen 16.

Figure 3:
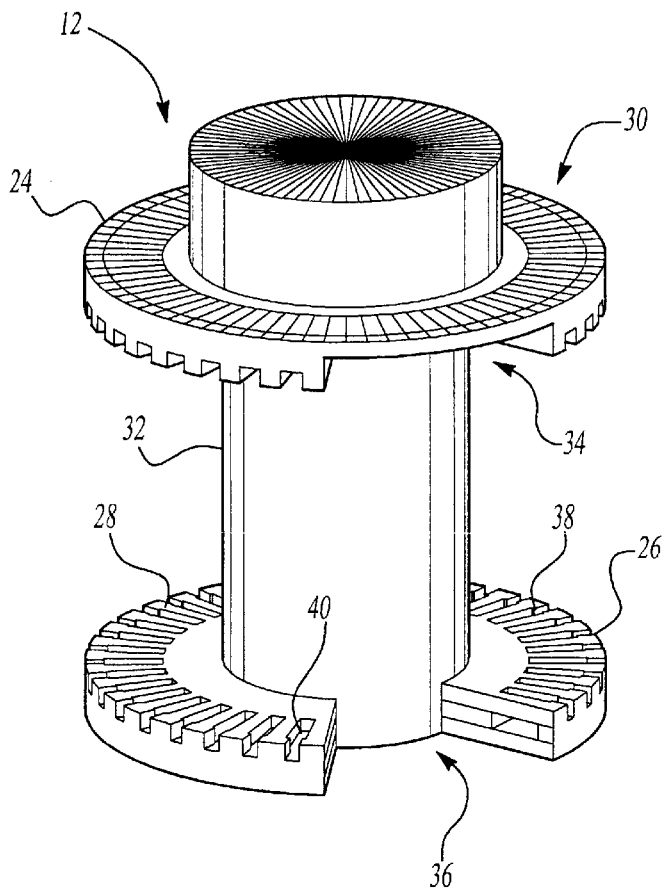
FIG. 3 is a perspective view of the slide storage device used in the staining system of the present invention.

The carousel 12, as illustrated in these drawings and in further detail in FIG. 3, has an upper portion 24 and a lower portion 26. The upper and lower portions are substantially identical in shape and size.

The upper and lower portions 24 and 26, respectively, each have an inner surface 28 and an outer surface 30. The inner surface 28 of the upper portion 24 faces the inner surface 28 of the lower portion 26. Centrally located in each of the portions is an aperture (not illustrated).

Located between the upper portion and lower portion is a hollow rod 32. The rod has a first end 34 and a second end 36. The first and second ends are received in the apertures, which are located in the upper and lower portion, respectively. The shaft of the first motor on the staining apparatus receives the hollow rod. This provides for the slide storage device to have a horizontally disposed central axis once it is secured to the shaft.

A plurality of radially oriented walls is provided along the inner surface of the upper and lower portion. These walls form a plurality of compartments 38. A retainer spring 40 is oriented between two adjacent walls for permitting releasable securement of the slide within the compartment. This retainer spring will permit for the carousal to accept slides of arbitrary thickness.

The slides are released, one at a time, from the storage device and onto the processing platen 16 via a slide transport apparatus 14. This slide transport apparatus comprises a first pair of conveyor belts 42 and a second pair of conveyor belts 44.

The design and structure of the conveyor belts permit a means of releasing the stained slides from the carousel and a means of transporting the slides to the various stations.

The first pair 42 of conveyor belts are parallel to each other and are located between the carousel and staining stations.

The second pair 44 of conveyor belts are parallel to each other and are located below and along the sides of the processing stations.

The first pair of conveyer belts extend around a first pulley 46 and a second pulley 48 (partly illustrated). The second pair of conveyor belts extend around a third pulley and a fourth pulley (neither illustrated). The first pulley is located within a housing 20 and is in the proximity of the carousel 12. The second pulley is located within the housing and is in the proximity of the first staining station. The third pulley is located next to the second pulley and the fourth pulley is located at the far end of the first platen.

The conveyor belts further include a plurality of evenly spaced rods or pips 50, which protrude vertically and beyond the processing stations. The rods or pips 50 in each pair of belts are in co-alignment. Once the apparatus is activated, the belts start to rotate about the pulleys. This provides for the rods or pips 50 from the first pair of belts 42 to push on the edge of a slide in the carousel 12. This causes the slide to be horizontally released from the carousel 12 and onto the belt 42 to provide for the specimen to be traveling in a downward position. A roller 52 is located adjacent to the carousel 12 to ensure that the slide in secured on the belt as it is released from the storage device 12.

While traveling on the first pair of conveyor belts 42, the slide will pass under an optical sensor (not illustrated). This optical sensor will initiate the count of the individually transferred slides as each slide engages onto the first belts 42 prior to the staining process. Optionally, this optical sensor can be replaced with a microswitch, in order to activate the unit.

The slide is then transported from the first pair of belts 42 to the second pair of belts 44 to permit for the rods or pips 50 from the second pair of belts 44 to aid in the transportation of the slide by driving it to the various processing stations.

A second motor (stepper motor) 54 is utilized to control and activate the first and second pairs of conveyor belts. This will provide for the slides to move at a constant rate of motion over the staining stations. The slide transport apparatus further includes an override switch for disengaging the stepper motor and stopping the movement of the slide transport apparatus when an alarm condition has been detected.

The processing platen 16 of the automated slide staining system 10 includes staining stations 18. The staining stations have a unique design and configuration. As illustrated in the figures (FIGS. 1 and 2), located at the corner of each station 18 is an aperture 56. These apertures 56 allow for a staining fluid to be dispensed in a capillary form between the underside of the slide and the upper surface of each staining station.

As further illustrated, the stations 18 are configured to be on the processing platen 16 at an acute angle. This acute angle aids in the flow of the staining fluid on the slide and also aids in the removal of the chemical as the slide is leaving the respective station.

The processing platen 16 further includes a plurality of troughs 58, which are situated between each station, and reservoirs (not illustrated), which are located in the front of the staining stations 18. A drainage orifice (not illustrated) is located within each reservoir. A waste tank (not illustrated) is underneath the first platen. This arrangement provides for the excess staining fluid from each station to flow into the troughs and to the reservoir. From the reservoir, the excess fluid flows into the waste tank via the drainage orifices. The waste tank can easily be removed from the housing via a first door 60. A display window 62 which is located on the front of the slide staining system 10, alerts the operator to empty and disposed of the fluid in the waste tank once a certain number of slides (i.e. 500) have been processed. The combination of the station being situated at acute angles and the location of the troughs provides for the staining fluid from the preceding station not to carry over to the succeeding station.

The last dispensing station 18a of the staining system dispenses a resin solution onto the slide. Adjacent to the last station is a heating station. After the resin solution has been dispensed onto the slide, it will travel to the heating station. The heating station consists of a convector 64, which will enable the resin solution to dry so that the tissue specimen, located on the slide, will be sealed. This seal creates a protective coating so that the specimen will be in a sterile and contaminant free environment.

From the heating station, each slide is directed to a slide receptacle 66. This slide receptacle receives and maintains the slides after a complete traverse of the slide staining stations.

The automated slide staining system also includes a fume extractor means. The fume extractor means removes the toxic fumes generated by the staining fluids during the dispensing cycle. The fume extractor means comprises of a plurality of openings 68, located above the staining stations, a charcoal filter within a housing 70, and an exhaust 72 having an exhaust fan. A cover or hood 74 is located above the staining stations 18 in order to trap the fumes from the staining solutions. This will enable them to be extracted from the area of the staining stations by way of the plurality of the openings 68. The charcoal filter absorbs the toxic fumes from the staining solution, while the exhaust fan which is controlled by a third motor 76, disposes the purified fumes from the automated slide staining system 10 via the exhaust 72.

The charcoal filter 70 can be remove and replaced simply by opening a second door 78 on the housing. This second door 78 exposes the filter's housing 70 and permits for it to be open so that the filter can be removed and/or replaced.

Figure 4:
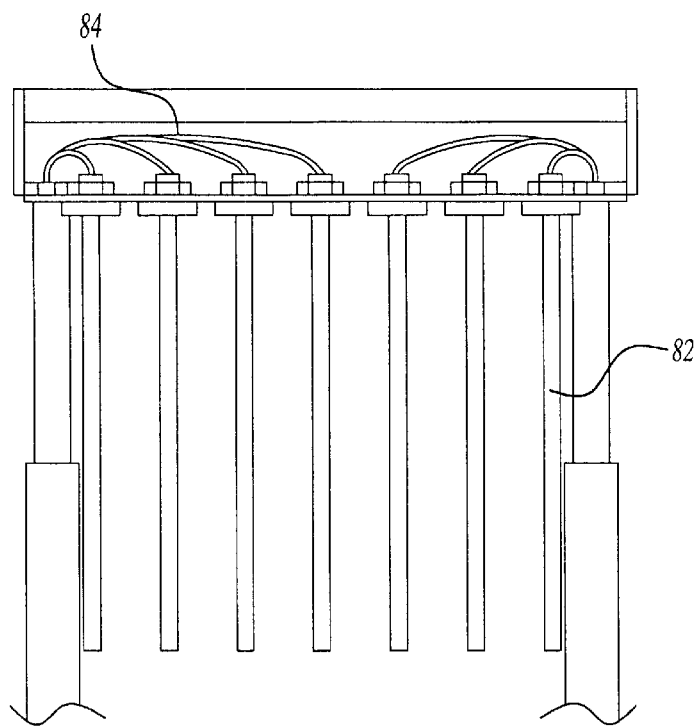
FIG. 4 is a front view of the cannula tubes used in the staining system of the present invention.

The staining fluid used in the automated slide staining system travels to its respective station via polytetraflouroethylene (PTFE or TEFLON) transfer tubings 80, as seen in FIGS. 2 and 4. Each tube comprises a first end and a second end. The first end is inserted to the underside of the staining station and into the aperture. The second end is attached to a cannula tube 82.

The cannula tubes 82 as illustrated in FIG. 2 and as further illustrated in FIG. 4 are inserted into a plurality of containers 84 containing a staining fluid. These tubes are connected to a pump 86 to permit for the staining fluid to flow from the cannula tube 82 to the aperture of the staining station via the transfer tubing 80. The pump is controlled by a fourth motor (illustrated but not labeled). The combination of the cannula tubes and the transfer tubing is also referred to as a channel. Each tubing is connected to a solenoid valve 88. The valve 88 controls the directional flow of the fluid. When the valve is in a closed position, the fluid is recirculating within the channel, while when the valve is in an open position, the fluid is diverted to the aperture within a station. When a slide is over the aperture of a particular station, a microprocessor activates the valve, for that particular station, to an open position. This will divert the fluid and provide for that fluid to be dispensed onto the particular station.

The second motor (stepper motor) is utilized for actuating the conveyor belts in order to guide the slides along the first platen of the staining system. A microprocessor (located within the electric bay 90) is used to count the steps or distance that each slide travels. When a slide reaches a particular and predetermined distance, the microprocessor will activate the solenoid valve so that the staining fluid for a particular station can be diverted to that station. The solenoid valve will remain open until the slide has traveled a certain or predetermined distance, at which time the microprocessor will send a signal to close the solenoid valve. This closure of the solenoid valve will provide for the fluid to recirculate within its respective channel.

Figure 5:
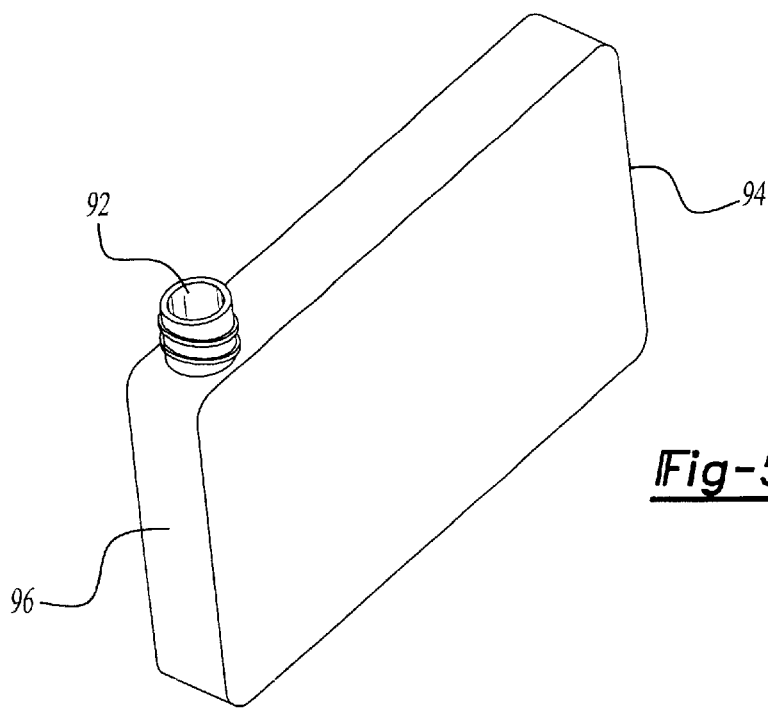
FIG. 5 is a perspective view of a bottle which is used to hold the staining fluids used in the automated slide staining system of the present invention.

The containers used for storing the respective staining fluids are provided with a unique shape and design. As illustrated in FIG. 5, each of the staining bottles includes an aperture 92 for receiving the cannula tube and two side walls 94, which are substantially longer than the front wall 96 and rear wall (not shown). The containers are placed in a box to provide for contact to be made with the container side walls (see FIG. 2). This box is placed within the housing via a third door 98 (see FIG. 1) of the automated slide staining system 10. This arrangement permits for the installation and replacement of the staining fluids to be made quickly and efficiently by removing the box holding the plurality of containers.

As illustrated in the various views of the automated slide staining system (FIGS. 1 and 2), the four digit LED display window 62 is located above the processing platen 16. Located in the proximity of the display window 62 is a plurality of keys or buttons 100. The keys or buttons represent the number of slides which are being processed in a particular batch 106, the speed of which the slides are traveling 104, and the number of slides which can be processed by utilizing the remaining staining fluid located in the containers 102. The four digit LED display window will enable an operator to display the desired key indication.

The speed at which the slides travel can be adjusted by the utilization of the speed button 104. This speed button will not only display the speed at which the slides are traveling, but will also permit the user to alter the speed. This change of speed will alter the intensity and contrast of the stain with respect to the tissue specimen.

In order to utilize the automated slide staining system of the present invention, an operator inserts stained slides into the compartments 38 of a storage device or carousel 12. The slides are secured in the storage device by springs 40, which are located inside each storage compartment.

The storage device is removably secured to a shaft. Once secured, the operator can then activate the power supply 108 of the staining system 10 by using a button to provide for the shaft to rotate, inherently causing the storage device 12 to rotate. The activation of the system will also initiate the conveyor belts 42 and 44.

The rods or pips 50 on the belts push or force a slide to exit the storage container 12. The slide is released from the storage container so that the specimen is facing in a downward position. The second motor 54 is used to control and operate the conveyor belts. The use of the first and second motors (stepper motors) and the arrangement and spacing of the rods or pips will permit for the slides to be released one at a time.

After release from the storage device, the slide first contacts an optical sensor (or optionally, a microswitch). The optical sensor (or optionally, the microswitch) initiates the count of the individually transferred slide. After contact with the optical sensor the slide is transferred to the staining stations 18 via the second set of conveyor belts 44.

The pulses that the microprocessor uses to drive a second motor 54 which powers the second set of conveyor belts are used to determine when the microprocessor will activate the solenoid valve for a particular station. Once a slide reaches a particular and predetermined distance, the microprocessor will transmit a signal to activate or open the solenoid valve of a particular station. This will enable the staining fluid to flow to the appropriate staining station. The solenoid valve will remain open until the slide has traveled a certain or predetermined distance, at which time the microprocessor will send a signal to close the solenoid valve.

The particular distance in this system for activation of the solenoid valve occurs when the slide is directly above the aperture in the station. The particular distance in which a signal will be transmitted to deactivate the system will occur when the slide exits that particular station.

The processing of the slides is continued until the slide reaches the heating station, which includes the convector 64. At this time the resin coating, which was applied at the last dispensing station 18a, is dried. This will provide for the slide to have a protective resin coating. After the resin has dried, the slide will be transported and dropped into a slide receptacle 66.

The automated slide staining system will continue to release the slides from the storage device. This will continue until all the slides have been released or if there is not a sufficient amount of staining fluid to process the slides.

In the above-described embodiment, a heating unit is provided after the last dispensing station. However, the automated slide staining system can be arranged such that a cover slip can be dispensed, one at a time, in order to apply it on a slide. This alteration is illustrated in further detail in FIGS. 6 and 7.

The cover slipper apparatus includes a separate platen 120, which is located in the proximity of the last station of the processing platen 16. This separate platen or transporting platen 120 includes a first end 122, a middle area 124, and a second end 126. This first end of the platen is at an obtuse angle with respect to the middle area. The first end 122 is located in the proximity above the distribution end of a dispenser tray 110, which houses the slides. The middle portion 124 to the second end of the transporting platen 120 is linear. The middle area of the platen is in the proximity of the processing platen 16. For enabling transportation of the cover slip and slide along the platen, a third pair of conveyor belts (illustrated, but not labeled) are located on the edge of the platen 120. Extending vertically and outwardly from these belts are a plurality of evenly spaced rods or pips (illustrated, but not labeled).

As also shown, the receptacle or dispenser tray 110 of the cover slip apparatus, which holds and maintains the cover slips provides for the cover slips to be held in a horizontally oriented position. This receptacle 110 can be secured to apparatus by the use of securing brackets (illustrated, but not labeled), a supporting platform 134, a combination thereof, or any conventional attaching means. Holding brackets, illustrated but not labeled, are not necessary for attaching the cover slip apparatus to the housing 20, but are necessary for maintaining the various components of the cover slip apparatus.

The holding receptacle 110 further includes an opened end which allows for the removal of the cover slips therein, thereby providing for the open end to face the processing platen 16. If a supporting platform 134 is utilized then the electrical components which control the cover slip apparatus are housed therein. Optionally, if the supporting platform is not used, then the electrical components which control the cover slip apparatus are housed within the housing 20 (illustrated in FIGS. 1 and 2).

A tension block 136 is slidably secured to the dispenser tray 110 for providing the cover slips to be held in position by the rear block which is pulled by a spring. Such an arrangement forces the slips to be pressed up against a pair of rollers, also known as the first roller and second roller.

Extending outwardly from the tension block 136 is a handle 138. A means can be provided for enabling the tension block to remain in a compressed state for loading. Such a means can be conventional, such as providing an extension that is adapted to contact the spring and allow the spring to be maintained in a compressed stated. The handle 138 permits the user to expose the dispenser tram for reloading of cover slips. Optionally, the tension block can be magnetically held in position in order to allow the user to quickly and efficiently fill the receptacle.

The cover slip apparatus of the present invention further includes a releasing means for releasing the cover slips from the holding receptacle. The releasing means includes a plurality of rollers.

A first roller or ejector roller 140, which is controlled by a first motor housed either in the housing 20 or in the platform 134, ejects or removes the cover slip from the receptacle to a second roller 142. This first roller 142 is located in front of the open end of the holding receptacle 110 and will contact the first or exposed cover slip. The second roller 142, like the first roller, is controlled by a second motor, also housed in the supporting platform 134 or housing 20. Once the cover slip reaches the second roller 142, the rotation of the first roller 140 ceases. Once this roller 140 ceases, the secondary roller 142 rotates in order to guide the cover slip to the third roller or positioning roller 144. This third roller or position roller 144 is fabricated from a durable and heavy material, such as stainless steel and is located above the secondary roller in order to ensure that the cover slip is properly positioned on the transport apparatus. As seen, this third roller 144 is maintained on a pair of slots (illustrated, but not labeled) and is therefore adapted to move freely along the slots.

Accordingly, when the cover slip approaches the third roller 144, it is displaced and will inherently push the cover slip forward and onto the first end 122 of the second platen 120. The slide, which includes the resin material, will contact the cover slip to provide for the cover slip to be secured to the slide. As the slide, having the cover slip attached thereto, approaches the second end 126, it is placed within a rack 146. The rack 146 is situated over a heating source 148 for adequately and efficiently drying the resin and securing the cover slip on the slide. The activation of the automated slide staining system will provide for the third set of conveyor belts to be activated. This activation will permit for the utilization of the cover slip apparatus.

To ensure that only one cover slip is dispensed, a pair of shafts (not illustrated), preferably fabricated from stainless steel, are mounted above the cover slip dispenser and above the first roller. The first shaft is mounted in a fixed position and the second shaft is mounted so that it's ends floats in respective C-shaped cups.

The first shaft, like the cover slips and rollers, is disposed horizontally and is aligned with the opened end of the holding receptacle. The second shaft is parallel to the first shaft and can move freely within the C-shaped cups. These C-shaped cups are secured to the bracket, illustrated, but not labeled. Hence, as the cover slip is removed, it extends between the two shafts. The upward motion of the cover slip forces the second shaft to move via the C-shaped cups. This movement causes a gap to be located between the first shaft and second shaft. The gap is of a sufficient dimension to enable only one cover slip to pass therethrough and to contact the second roller.

Figure 6:
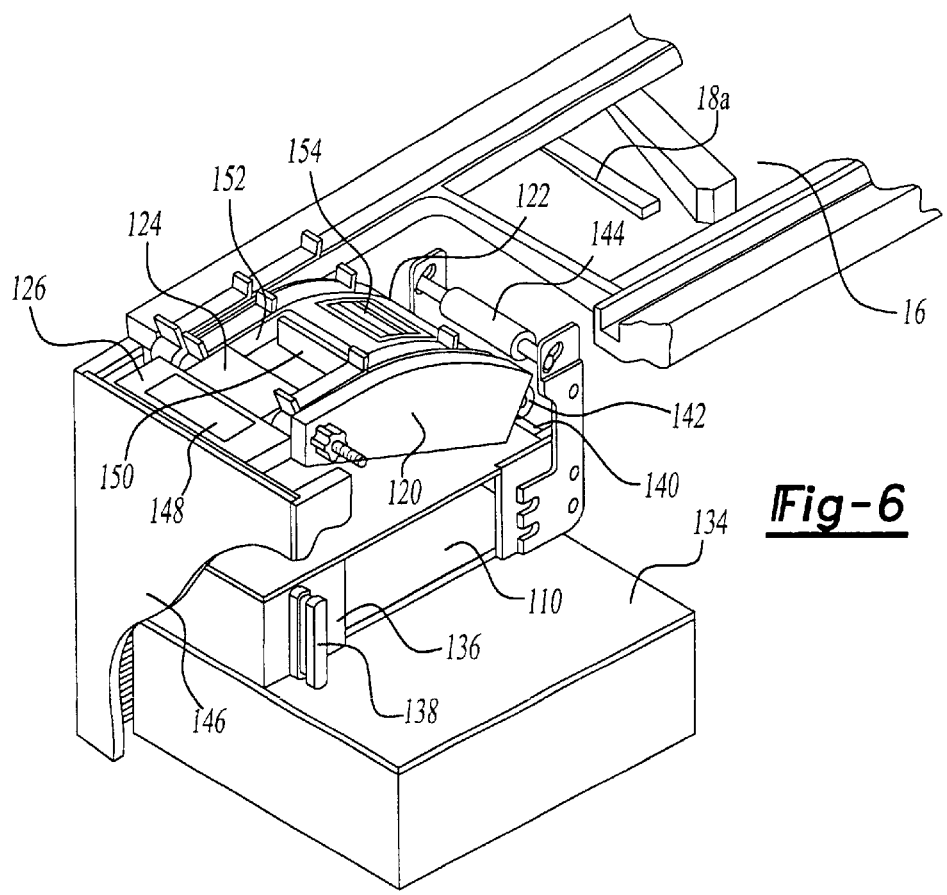
FIG. 6 is an enlarged view of the cover slip apparatus used in the second embodiment of the present invention.

As illustrated in further detail in FIG. 6, the cover slip apparatus includes an additional safety measure by providing a means of removing resin if a cover slip is not introduced onto the slide. This resin removing means comprises a bar 150 located at a distant end of reservoir 152. As the slide having no cover slip attached thereon contacts the bar 150, the resin will be scraped and transferred into the reservoir 152. The ends of the bar 150 will allow gravity to force the resin down into the reservoir 152. This bar can be designed such that it includes tapered ends. This will provide for the bar to have a tip and the tip portion can be-used to scrap the resin. The tapered ends will guide the excess resin down into the respective reservoir.

For added security, the cover slip apparatus further includes a neutralizing means 154 for dissipating any potential electrostatic charge, which may occur, as the cover slip is removed from the receptacle 110. This neutralizing means 54 is conventional and can include any commercially available and safe radioactive product.

Figure 7:
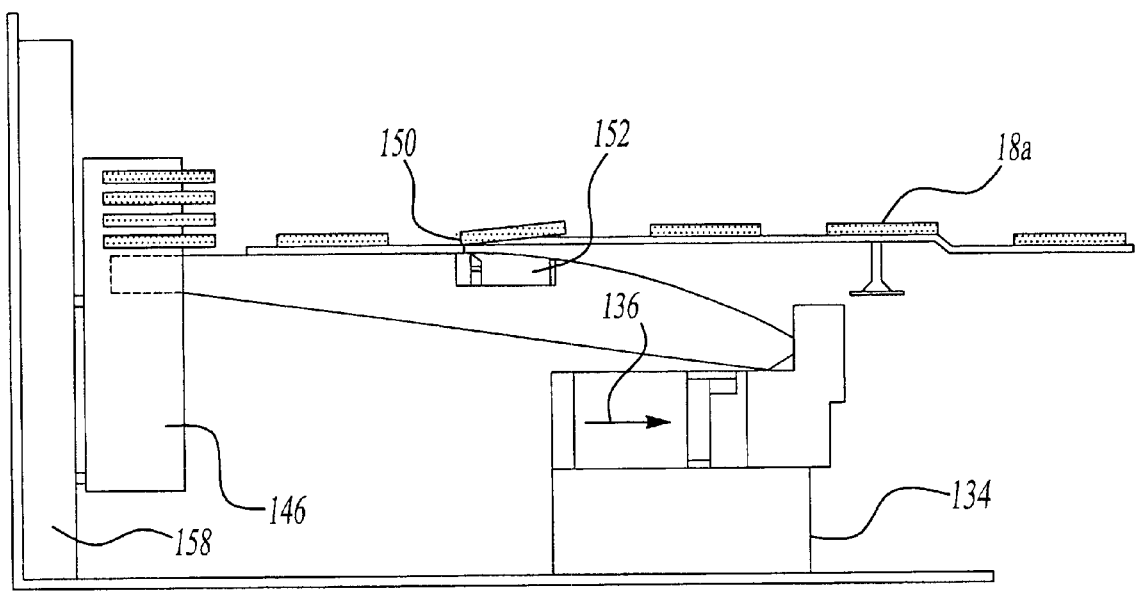
FIG. 7 is a side view of the cover slip apparatus having the rack secured thereto, used in the second embodiment of the present invention.

The rack is illustrated in further detail in FIGS. 6 and 7. As seen in these drawings, the rack 146 is located at end of the cover slip apparatus. This design and configuration will allow for the covered slides to be stored safely therein. Located on the outer end of the cover slip apparatus, on the opposite end of the releasing means, is a conventional heating unit 156. This heating unit 156 will supply appropriate heat for adequately and efficiently drying and curing the resin. This will provide for the cover slip to be secured to the slide.

The storage rack 146 is controlled by a storage rack drive unit 158. This unit 158 is coupled to the rack 146 and enable the rack to shift upward once a slide is located therein. The unit 158 is conventional and permits for the apparatus to extend upwards accordingly. An optical sensor is located within the storage rack drive unit 158 for sensing and detecting when the rack should be incremented.

This second embodiment further includes a second sensor, which will detect when the cover slip dispenser tray is empty. If the dispenser tray is empty, a warning will be displayed on the front panel of the LED display window.

It is noted that in order to ensure the contact between the cover slip and slide, the last station 18a is situated below the other stations. This design and configuration will provide for a gap to exist between the stained slide and station. The resin is then dispersed quickly from the apertures (illustrated, but not labeled).

Preferably, the apertures on the last station are so designed so that two drops are dispersed on the lower surface of the slide. A separate pump is used for dispersing the resin. This separate pump can be located within the housing 20. The apertures for the last station are sized such that a minimal amount of resin is extracted therefrom. A size for the apertures of approximately 0.013 inches in diameter has been used successfully.

The utilization of the automated slide staining system in conjunction with the present invention is similar to the use of the system with the heating station, except that in this embodiment the heating station is replaced with the cover slip storage and dispensing apparatus. In this embodiment, the processing of the slides is continued until the slide reaches the cover slip apparatus. At this time the resin coating, which is preferably distributed utilizing two apertures, applied at the last dispensing station, acts as an adhesive for the cover slip.

As the slide comes into the cover slip area, the microprocessor, or optionally, an optical sensor, detects its presence of the slide and will send a signal for proper activation of the cover slip apparatus. This signal will activate the first motor. This motor turns the first roller. Since this roller contacts the first exposed cover slip as it rotates, clockwise, it inherently lifts the front cover slip. This cover slip then contacts the parallel shafts. As it moves upwards via the first roller, it forces the second shaft to move causing a gap to be located between the first and second shaft. The cover slip passes through the two shafts. This gap is of a dimension wherein only one cover slip can extend therethrough. The gap is set by feeler gages, preferably, to 0.008 inches.

When the first motor completes one revolution, an optical switch detects a slot cut in the flange of the pulley mounted on the motor drive shaft. This optical switch activates the electronics for deactivating the first motor and activation the second motor. The deactivation will cease rotation of the first roller while the activation of the second motor will cause the second roller to activate. At this point the cover slip has been dispensed in an upward direction by the first roller and through the pair of shafts.

This second roller and the entire cover slipper dispenser are mounted so as to be in contact with the third roller. Since the third roller is an idler roller mounted at the end of the cover slipper platen, it will consequently position the cover slip accordingly. As the second motor drives the second roller in a clockwise direction, it lifts the cover slip upward. At this point the cover slip is still being dispensed in a vertical direction. As it passes through the second roller it has to be tilted to the left so that it will lay at an angel of approximately 25 degrees onto the cover slipper platen, where it can be picked up by the drive belts and transported up to meet an oncoming slide.

To achieve this action there, the third or free floating roller is utilized. As the slide is lifted up it moves this roller backwards in its slots. As soon as the slip is clear of the second roller, the weight of the free floating roller is sufficient to force the slip to tilt over and lay on the platen.

The slip once ejected is guided into position on the cover slipper platen by an angled side on the platen. This forces the slip, as it is picked up by the belt's pips, to move into its correct position. The slip is then transported up the cover slipper platen at an angle to the oncoming slide that is to be cover. The oncoming slide at the last station of the platen has received two jets of resin. These two jets have deposited two drops of resin to the underside of the slide. The slide continues with the two drops until it reaches a section of the rails, along which it is traveling, where it is tilted down very slightly at its front edge. This action allows the drops to run forward towards the front edge of the slide. At this point the cover slip leading edge is also very close to the leading edge of the slide, but still at a slight angle to it. The drops of resin catch the cover slip and form a pool of liquid at the leading edge of the slide and slip. The resin is held between these two surfaces by surface tension. As the slide and slip proceed further the angle of the slip is further decreased and capillary action takes over causing the resin to flood rearwards across the face of the slide and slip. This action also causes the slip to be pulled up onto the slide. This action also causes any air to be pushed out by the action of the resin flooding across the slide, so that no air bubbles are trapped between the glass surfaces. The action of the resin flowing from front to rear across the face of the slide causes an equal and opposite effect as in Newton's Laws of motion, thus allowing the slip to move from just rear of the front of the slide to actual being centered on the slide.

The cover slipped slide is then transported to the end of the platen where it is loaded into a pair of slots in the rack collection unit. It finally stops being moved once it is entered into the rack and it comes to rest over a heater plate. The heater dries the edges of the slide and slip sufficiently to hold the two in place. The resin contains Toluene, which will evaporate quickly at a low temperature. The rack is incremented up one pair of slots at a time to allow the slide to be loaded into it in the same sequence as they left the carousel. At the end of a run, the rack can be removed with the slides in it and taken for reading, as these are completely processed slides. The process is continued until the rack is completely occupied or the cover slip receptacle or is emptied.

It is noted that the size of each station and the number of stations used in the first or second embodiment can be changed in order to accommodate the testing that is desired (i.e. histology versus cytology).

The method involved in the processing of a histology tissue specimen using the automated slide staining system of the present invention includes a plurality of different solutions to be dispensed at each station. At the first station, the paraffin is removed from the tissue by the use of xylene. The specimen is then hydrated with ABS alcohol (second station) followed by a hydration of diluted alcohol (third station). The cell nuclei of the specimen are then treated with a hematoxylin compound (fourth station). The next step is to remove the excess stain from the specimen using a diluted acid compound (fifth station). The specimen is dehydrated by using a pure alcohol (sixth station). The enhancing of the nuclear stain contrast with respect to the specimen using a dilute alkali solution (seventh station). The specimen is then dehydrated by the use of pure alcohol (eighth station). The specimen is then stained for cytoplasm by using an eosin compound (ninth station). Again the specimen is dehydrated, this time by the use of ABS alcohol (tenth station). Further dehydration of the specimen occurs with a solution of 50 percent ABS alcohol and 50 percent xylene (eleventh station) The specimen is cleaned using a xylene solution (twelfth station). At the last dispensing station, a coating is applied to the slide for maintaining the specimen to be in a contamination free status (thirteenth station).

From the last dispensing station, the slide is either transported to a drying station or to a cover slip area.

The method involved in the processing of a cytology tissue specimen using the automated slide staining system of the present invention includes a plurality of different solutions to be dispensed at each station. At the first station, the specimen is hydrated with an alcohol solution. The specimen is hydrated again with a second alcohol solution (second station). The plurality of cell nuclei of the tissue specimen is processed with a hematoxylin stain compound (third station). Excess staining material is then removed from the specimen with a diluted acid solution (fourth station). The specimen is dehydrated with an alcohol solution (fifth station). The next step is for enhancing the nuclear staining contrast of the tissue specimen with a dilute alkali solution (sixth station). The specimen is dehydrated with an alcohol solution (seventh station). The next step is to counterstain the specimen for highlighting cytoplasmic cell material (eighth station). The removal of the excess staining material from the tissue specimen is the next step (ninth station). Counterstaining the specimen for cytoplasmic cell contrast then occurs (tenth station). The specimen is then dehydrated with ABS alcohol (eleventh station). Further dehydration of the specimen occurs with a second dispensing of ABS alcohol (twelfth station). Optionally, at this twelfth station, the specimen can be dehydrated with a solution of 50 percent ABS alcohol and 50 percent xylene. The specimen is then cleaned with a xylene compound (thirteenth station). At the last dispensing station, a coating is applied to the slide for maintaining the specimen to be in a contamination free status (fourteenth station).

From the last dispensing station, the slide is either transported to a drying station or to a cover slip area.

Figure 8:
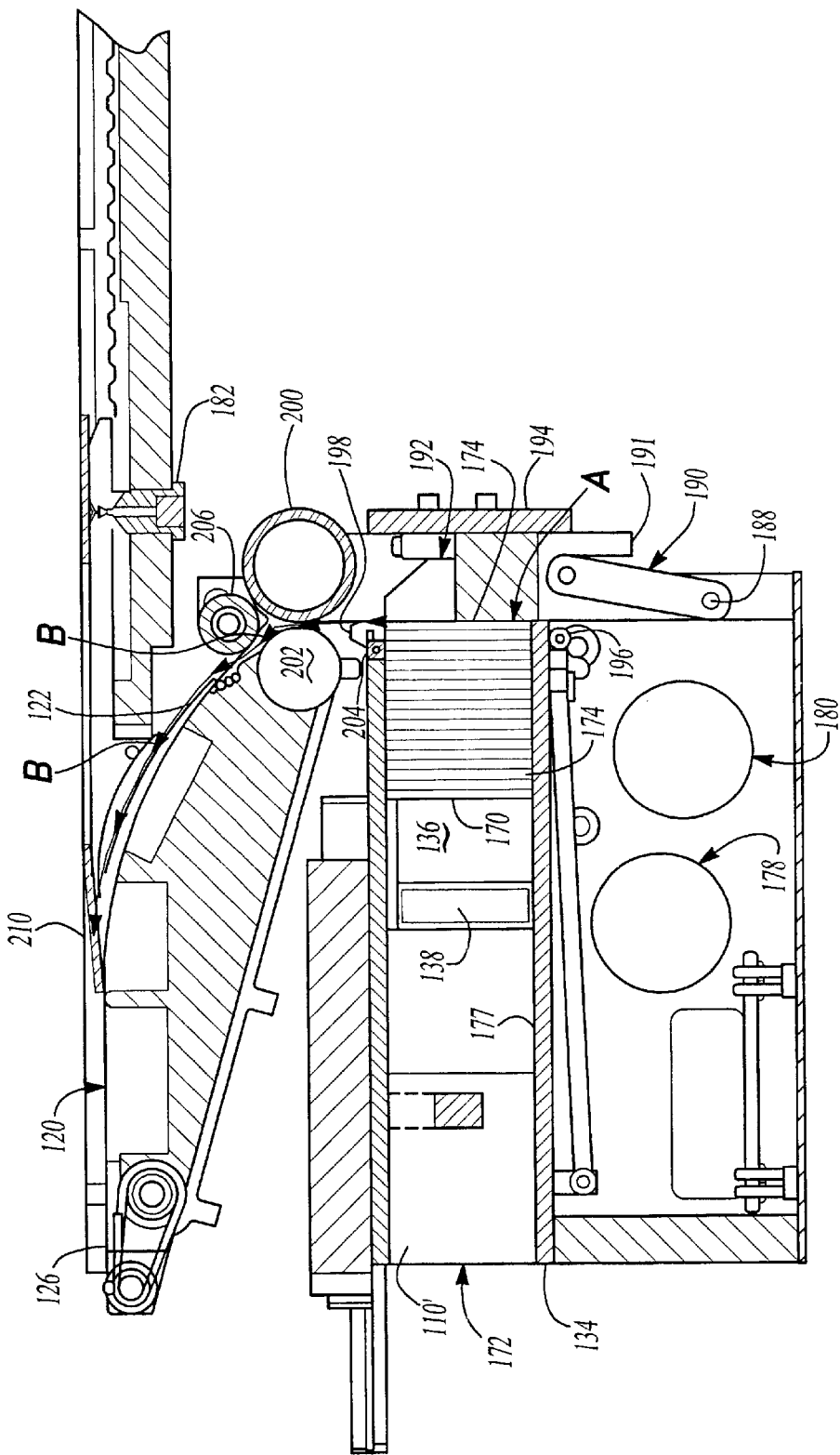
FIG. 8 is a cross-sectional view of the cover slip apparatus used in a further embodiment of the present invention.
Figure 9:
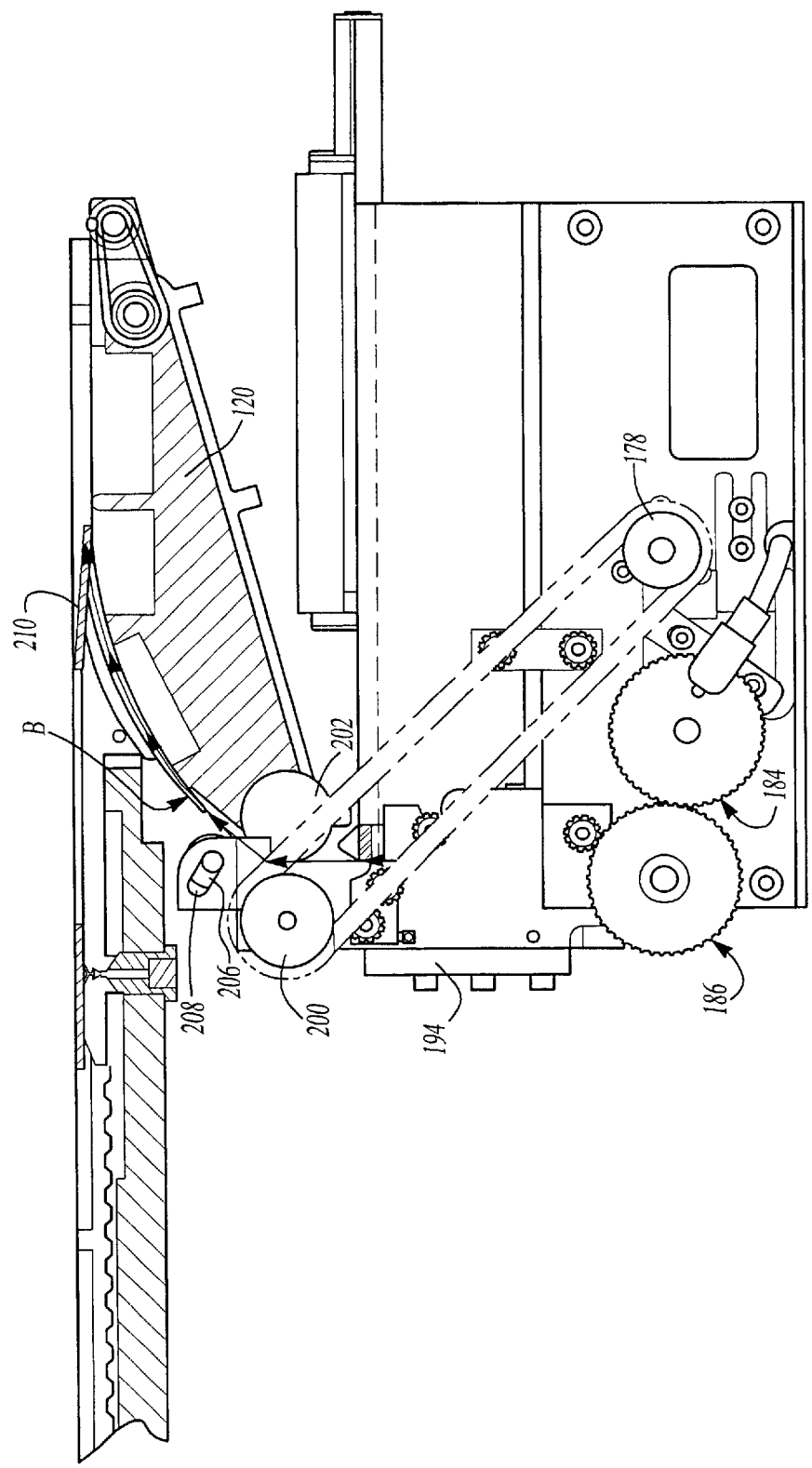
FIG. 9 is another cross-sectional view of the cover slip apparatus used in a further embodiment of the present invention.
Figure 10:
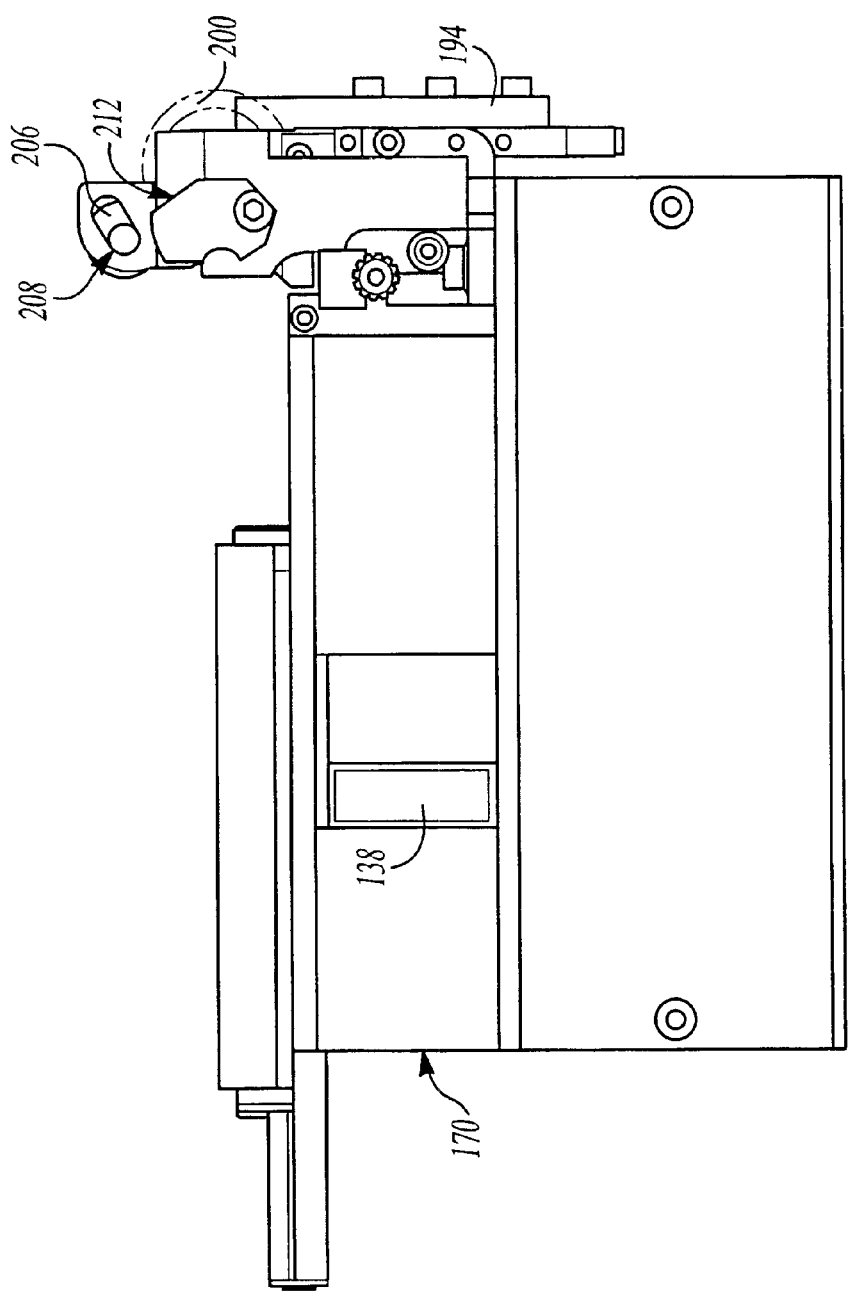
FIG. 10 is a side view of the cover slip apparatus with an optical sensor attached thereto.

A further embodiment of the invention is illustrated in FIGS. 8 through 10. FIGS. 8 through 10 illustrate an alternative approach for dispensing a cover slip 170 one at a time by way of a cover slipper apparatus 172. As in the embodiment of FIGS. 6 and 7, cover slipper apparatus 172 includes a separate platen called a transporting platen 120 that is located in the proximity of the last station of the processing platen 16. Transporting platen 120 includes a first end 122, a middle area 124, and a second end 126.

A receptacle or dispenser tray 110' of the cover slip apparatus 172, which holds and maintains cover slips 170, provides for the cover slips to be maintained in a rest position in a vertical orientation with a face of a first cover slip in facial contact with a front wall 174 of tray 110'. Thus, a first edge 176 of each cover slip 170 contacts the floor 177 of tray 110' before it is placed in a dispensing position for release as described below. As in FIGS. 6 and 7, tray 110' may be secured to the apparatus by the use of securing brackets, a supporting platform 134, a combination thereof, or any conventional means. If a supporting platform 134 is utilized then electrical components such as motors 178 and 180 are housed therein. Optionally, if the supporting platform 134 is not used, then the electrical components that control the cover slip apparatus are housed within housing 20 (illustrated in FIGS. 1 and 2).

A tension block 136 with a handle 138, as described above, is slidably secured to tray 110 for providing the cover slips to be held in position such that the slips are held in their vertical orientation between front wall 174 and tension block 136.

As a slide comes into the cover slip area, an adhesive resin is dispensed in the form of drops, via two jets 182, to the underside of the slide. The microprocessor then signals for the dispensing of a single cover slip 170.

As in FIGS. 6 and 7, tray 110' includes an opened end that acts as a release point and allows for the dispensing of the cover slips 170 therein. However, the release mechanism for dispensing a cover slip is different. Motors 178 and 180 begin to turn. Motor 178 turns drive gear 184, which is in engagement with and thereby turns mating gear 186. Gear 186 is pivotally connected to a first opposing end 188 of a linear crank mechanism 190. In turn, a second opposing end 191 of crank mechanism 190 is pivotally connected to a slip lift 192 acting as an ejector. Slip lift 192 is constrained between tray 110' and a fixed vertically extending wall 194 such that it only can go up and down in response to circular movement of gear 186. Thus, crank mechanism 190 is used to convert rotational movement into linear movement.

Slip lift 192 includes a side surface that acts as front wall 174 of tray 110 and includes a very narrow ledge 196 at a bottom surface thereof, the ledge being generally perpendicular to front wall 174. In a rest position as shown in FIG. 8, ledge 196 is generally flush with or slightly below floor 177 of tray 110'. It must not be above the surface of floor 177 or the next available cover slip 170 cannot be advanced for release. The width of ledge 196 is carefully controlled so as to correspond to the width of a single cover slip 170. Gear 186, crank mechanism 190 and slip lift 192 are carefully sized such that as gear 186 rotates, a single cover slip 170 is vertically lifted out of tray 110' in the direction of arrow A. When gear 186 rotates one-hundred and eight degrees (180°) from its rest position to an ejecting position, slip lift 192 is at its highest vertical position and a cover slip sufficiently clears tray 110' to engage a transport mechanism as discussed further below.

As a further precaution against more than one cover slip 170 from being dispensed at a time, a very narrow gap exists between wall 174 and a stripping bar 198. Wall 174 and stripping bar 198 act as a cover slip metering device in a manner similar to that discussed with respect to FIGS. 6 and 7. Preferably, the stripping bar 198 is adjustable. In a preferred embodiment, the stripping bar 198 is adjusted to provide approximately a 0.009" (0.23 mm) opening with respect to wall 174 such that only a single cover slip 170 may pass there between. If two cover slips 170 are stuck together, the use of stripping bar 198 helps to separate the two covers lips.

Once a cover slip 170 exits tray 110' and passes by stripper bar 198, it comes into contact with a transport mechanism including a fixed driven roller 200, which is driven by motor 180. A biased idler roller 202 opposes driven roller 200 and is in selective frictional engagement with it. Rollers 200 and 202 are positioned so that a covers slip 170 vertically exiting tray 110' will engage the mating point between the two rollers to minimize unwanted initial distortion and to prevent accidental jamming upon removal from tray 110'. Since idler roller 202 is biased, cover slip 170 is able to pass through the mating point where the driven roller then propels the cover slip away from tray 110'. A free edge 204 of the cover slip 170 opposing edge 176 passes through the mating point between rollers 200 and 202. However, as soon as free edge 204 passes through the mating point, it must be tilted so that it will lay at an angle of approximately twenty-five degrees (25°) on the transporting platen 120 as shown by arrows B, where it can be picked up by the drive belts acting as a drive mechanism and transported up to meet an on coming slide at a merge point as discussed above. To achieve this, a free-floating roller 206 is used. As the cover slip is lifted by slip lift 192 and passes through mating rollers 200 and 202, roller 206 is moved backwards in a slot 208 with a substantial vertical component. Roller 206 is given sufficient weight such that as soon as free edge 204 is clear of roller 202, the weight is sufficient to force the cover slip 170 to tilt over and lay on transporting platen 120. Then the pips of the conveyor belt, take over and cover slip 170 is transported up platen 120 as discussed above with respect to FIGS. 6 and 7 so that it merges with an oncoming slide that is to be covered at merge point 210.

To verify that the cover slipper mechanism 172 is properly dispensing cover slips 170, it is preferably equipped with an optical sensor 212 as best shown in FIG. 10. Sensor 212 monitors the movement of roller 206, which must move if a slip is dispensed. If no movement is detected in the time period required to dispense two slips, then the device goes into an error mode. When an error mode is triggered through a problem with the cover slipper mechanism 172, the following actions preferably take place: (i) an audible alarm signals the operator and an appropriate message concerning a problem with mechanism 172 is displayed; (ii) the cover slipper 170 stops dispensing slips; (iii) jets 182 are disabled; (iv) no additional slides are dispensed from storage device or carousel 12 (shown in FIG. 1); and (v) all slides that are in process on the platen 16 are completed without a cover slip 170. Once the problem is corrected, the system is reset and normal operation continues.

While the invention has been particularly shown and described with reference to an embodiment thereof, it will be understood by those skilled in the art that various changes in form and detail may be made without departing from the spirit and scope of the invention.

What is claimed is:

1. A cover slip apparatus for use with a slide of a slide staining system, comprising:
   a receptacle for storing a plurality of cover slips, wherein said receptacle includes an opening and a slip lift adapted to be in contact with a first exposed cover slip to selectively eject the cover slip from said receptacle;

a release mechanism for dispensing cover slips one at a time from a release point associated with said opening within said receptacle, said release mechanism including an ejector to selectively advance cover slips one at a time from a rest position;

a transport mechanism comprising a plurality of rollers adapted to receive a cover slip from said release mechanism;

a drive mechanism associated to receive a cover slip from said transport mechanism and advance it away from said transport mechanism and said receptacle; and a slide merge point positioned adjacent a termination point for said drive mechanism and away from said release point.

2. A cover slip apparatus as recited in claim 1, where said slip lift includes a ledge adapted to engage a bottom edge of the first exposed cover slip.

3. A cover slip apparatus as recited in claim 2, wherein said ledge is adapted to be approximately the width of a cover slip.

4. A cover slip apparatus as recited in claim 1, said apparatus further including:

a motor;

a gear in rotating engagement with said motor; and a crank mechanism having a first end in pivoting engagement with said gear and a second end in pivoting engagement with said slip lift to convert rotational motion of said gear into linear motion of said slip lift.

5. A cover slip apparatus as recited in claim 1, wherein said slip lift is restrained to only move linearly between a rest position and an ejecting position.

6. A cover slip apparatus as recited in claim 2, wherein an inner surface of said ledge is adapted to be substantially flush with or below a floor of said receptacle.

7. A cover slip apparatus as recited in claim 1, wherein a cover slip metering device is disposed between said release mechanism and said transport mechanism.

8. A cover slip apparatus as recited in claim 7, wherein said cover slip metering device comprises at least two opposing elements defining, a gap therebetween such that only one cover slip may pass through said gap from said release mechanism to said transport mechanism.

9. A cover slip apparatus as recited in claim 8, wherein said gap is in the range of approximately 0.008 to 0.009 inches.

10. A cover slip apparatus as recited in claim 1, wherein a first roller of said transport mechanism selectively receives each released cover slip from said release mechanism, and rotates to advance it along a predetermined path away from said release point and toward said merge point.

11. A cover slip apparatus as recited in claim 10, wherein said first roller is generally aligned with said release mechanism to maintain the initial direction of motion for each cover slip upon movement from said release point to minimize unwanted initial distortion and to prevent accidental jamming upon removal from said receptacle.

12. A cover slip apparatus as recited in claim 1, wherein a roller of said transport mechanism selectively receives each cover slip, and displaces it from said initial direction of motion to be advanced toward said merge point.

13. A cover slip mechanism as recited in claim 12, wherein said roller is biased toward a rest position.

14. A cover slip mechanism as recited in claim 13, further including a sensor, said sensor noting movement of said roller away from said rest position toward an activation position, and selectively issuing an alarm if said roller does not move away from said rest position after a predetermined period of time.

15. A cover slip apparatus for use with a slide of a slide staining system, comprising:

a receptacle for storing a plurality of cover slips, wherein said receptacle includes an opening for selectively dispensing each cover slip one at a time;

a release mechanism for dispensing cover slips one at a time from a release point within said receptacle, said release mechanism including a fixed member and an opposing movable member with an ejector to selectively advance cover slips one at a time from a rest position;

a transport mechanism comprising a plurality of rollers adapted to receive a cover slip from said release mechanism, a first roller selectively receiving each released cover slip from said release mechanism and advancing it along a predetermined path away from said release point;

a cover slip metering device disposed between said release mechanism and said transport mechanism comprising at least two opposing elements defining a gap therebetween such that only one cover slip may pass through said gap;

a drive mechanism to receive a cover slip from said transport system and to advance it away from said transport mechanism and said receptacle; and a slide merge point positioned adjacent a termination point for said platen drive mechanism and away from said release point, where said receptacle includes a slip lift adapted to be in contact with a first exposed cover slip to selectively eject the cover slip from said receptacle, where said slip lift includes a ledge adapted to engage an edge of the first exposed cover slip, and wherein an inner surface of said ledge is adapted to be no more than substantially flush with a floor of said receptacle.

16. A cover slip apparatus as recited in claim 15, said apparatus further including:

a motor;

a gear in rotating engagement with said motor; and a crank mechanism having a first end in pivoting engagement with said gear and a second end in pivoting engagement with said slip lift to convert rotational motion of said gear into linear motion of said slip lift, wherein said slip lift is restrained to only move linearly between a rest position and an ejecting position.

* * * * *